United States Patent [19]
Tovey et al.

[11] Patent Number: 5,441,044
[45] Date of Patent: Aug. 15, 1995

[54] SURGICAL RETRACTOR

[75] Inventors: H. Jonathan Tovey, Mildord; Gary S. Kappel, Stamford, both of Conn.

[73] Assignee: United States Surgical Corporation, Norwalk, Conn.

[21] Appl. No.: 108,140

[22] Filed: Aug. 16, 1993

[51] Int. Cl.$^6$ ............................................. A61B 17/02
[52] U.S. Cl. ................................. 600/234; 606/198; 600/215
[58] Field of Search ................. 128/20; 606/47, 106, 606/107, 127, 191, 198, 114, 113; 604/104, 105

[56] References Cited

U.S. PATENT DOCUMENTS

| | | |
|---|---|---|
| 972,983 | 10/1910 | Arthur . |
| 1,328,624 | 1/1920 | Graham . |
| 3,467,079 | 9/1969 | James . |
| 4,190,042 | 2/1980 | Sinnreich . |
| 4,459,978 | 7/1984 | Kotsanis . |
| 4,654,028 | 3/1987 | Suma . |
| 4,718,419 | 1/1988 | Okada ........................ 606/47 |
| 4,744,363 | 5/1988 | Hasson . |
| 4,791,924 | 12/1988 | Kelman . |
| 4,905,423 | 3/1990 | Van Laere ................. 310/47 X |
| 4,909,789 | 3/1990 | Taguchi et al. . |
| 4,934,352 | 6/1990 | Sullivan, Jr. ................... 128/20 |
| 5,113,846 | 5/1992 | Hiltebrandt et al. .............. 128/20 |
| 5,178,133 | 1/1993 | Pena . |
| 5,195,505 | 3/1993 | Josefsen . |
| 5,195,507 | 3/1993 | Bilweis ........................ 128/20 |
| 5,199,419 | 4/1993 | Remiszewski et al. . |
| 5,203,786 | 4/1993 | Vernick . |
| 5,325,848 | 7/1994 | Adams et al. ................... 128/20 |
| 5,352,237 | 10/1994 | Rodak et al. ................ 128/20 X |
| 5,353,784 | 10/1994 | Nady-Mohamed ............. 128/20 |
| 5,358,496 | 10/1994 | Ortiz et al. ................... 606/198 |
| 5,368,597 | 11/1994 | Pagedas ....................... 606/114 |

FOREIGN PATENT DOCUMENTS

| | | |
|---|---|---|
| 736949 | 7/1977 | U.S.S.R. . |
| 1360708 | 7/1986 | U.S.S.R. . |
| WO9102493 | 3/1991 | WIPO . |

Primary Examiner—Richard J. Apley
Assistant Examiner—Donna L. Maraglio

[57] ABSTRACT

A surgical retractor is provided for manipulating body tissue during endoscopic and laparoscopic surgical procedures which includes a handle assembly, an elongated body extending from the handle assembly, and a retractor assembly operatively associated with the body and defining a curvilinear tissue manipulation surface having an area which is selectively variable. In operation the retractor assembly is movable between a first position wherein the area of the tissue manipulation surface is minimized and a second position wherein the area of the tissue manipulation surface is maximized. The retractor can be designed for one handed operation.

30 Claims, 5 Drawing Sheets

SURGICAL RETRACTOR

BACKGROUND OF THE INVENTION

1. Field Of The Invention

This invention relates to surgical instrumentation and, more particularly, to a surgical retractor which includes a tissue manipulation surface having an area which is selectively variable for manipulating tissue and organs during endoscopic or laparoscopic surgical procedures.

2. Description of Related Art

Most endoscopic or laparoscopic procedures are characterized by the provision of an elongated cannula structure having a relatively thin diameter with a proximal and distal end. The distal end is passed through the surrounding tissue, such as the peritoneum, into a body cavity wherein the surgical procedure or examination is to be effected, thus providing a conduit for the insertion of surgical instrumentation. A plurality of cannula structures may be used to allow operation of a variety of instruments simultaneously during a given procedure.

In conventional surgical procedures the function of holding tissue and organs in a given location to facilitate access and viewing is typically accomplished by a retractor. This instrumentation is typically in the form of a broad paddle structure or multiple fingers attached to a handle. See, for example, U.S. Pat. No. 3,467,079 to James. This structure, however, is not usable in endoscopic procedures because the retractor is too large to be insertable through the cannula structure into the operative body cavity.

Collapsible intralumen expanders or retractors have taken the form of radial fingers which are activatable to extend relative to each other upon entering the body cavity. See, for example, U.S. Pat. No. 4,654,028 to Suma, U.S. Pat. No. 4,459,978 to Kotsanis, and U.S. Pat. No. 4,909,789 to Taguchi et al. Dilators of this type are also known in the art. See, for example, U.S. Pat. No. 1,328,624 to Graham and U.S. Pat. No. 972,983 to Arthur. In each case, once the retractive or dilatory function is completed, the fingers are compressed and withdrawn.

Other collapsible retractor instruments include collapsible fingers joined by webs of resilient material which, upon insertion into the abdominal cavity through a cannula, expand to form a retractive structure. See, for example, U.S. Pat. No. 4,190,042 to Sinnreich and U.S. Pat. No. 4,744,363 to Hasson. Another surgical retractor having an expandable frame for supporting an expandable latex sheath is described in U.S. Pat. No. 5,178,133 to Pena.

Other surgical apparatus having deployable interleaved retractor blades have been described in Soviet references. See, for example, SU 736-949 which describes an instrument having an elongated housing with a plurality of blades operative at one end by means of a manipulator at the opposed end, and SU 1360-708-A which describes an instrument having a plurality of interleaved blades which cannot be manipulated at a distance and thus is unsuited for performing endoscopic or laparoscopic procedures.

Greatly improved retractor instruments have been developed and are described in commonly assigned U.S. Pat. Nos. 5,195,505 to Josefsen, and 5,199,419 to Remiszewski et al. Both of these patents describe retractor structures which include a plurality of interleaved retractor blades mounted in a tubular housing. The blades are movable between a closed position and an open position to facilitate ease of insertion and deployment through a cannula.

Despite this wide variety of available endoscopic or laparoscopic instrumentation, there remains a need for instruments that are easily manipulable and can be deployed with one hand. There is also a need for instruments that can be selectively deployed to a multiplicity of positions between a closed position and an open position. Furthermore, there is a need for endoscopic or laparoscopic retractor that incorporate the above features.

SUMMARY OF THE INVENTION

The subject invention provides a surgical retractor for manipulating body tissue during endoscopic and laparoscopic surgical procedures which is uniquely configured to be operated with only one hand. The instrument includes a handle assembly, an elongated body extending from the handle assembly and defining a longitudinal axis, and a retractor assembly operatively associated with the body and defining a curvilinear tissue manipulation surface having a boundary portion which is substantially collinear with the elongated body. In use, the retractor assembly of the subject invention is movable from a first position wherein the area of the tissue manipulation surface is minimized to a second position wherein the area of the tissue manipulation surface is maximized.

In a preferred embodiment of the subject invention, the area of the curvilinear tissue manipulation surface of the retractor assembly is selectively variable through operation of an actuation assembly remote from the surgical site. The retractor assembly is therefore movable to a multiplicity of positions, ranging from a first position wherein the area of the tissue manipulation surface is minimized to a second position wherein the area of the tissue manipulation surface is maximized. Preferably, the actuation assembly is configured to be operated by the surgeon with one hand, leaving the second hand free to operate other instrumentation.

The surgical retractor of the subject invention also preferably comprises means for biasing the retractor assembly toward the second position. Control means are provided for selectively controlling the biasing means to permit gradual movement of the retractor assembly from the first position to the second position. Preferably, the control means comprises a selectively engagable ratchet assembly adapted to overcome the biasing force of the biasing means to maintain the actuation assembly in a desired position corresponding to a specific configuration of the retractor assembly.

Preferably, the retractor assembly includes first and second boundary members which define the periphery of the tissue manipulation surface, and an expandable elastomeric membrane which occupies the area bounded by the boundary members. The first boundary member is preferably formed of a resilient material having a preformed curved configuration and the second boundary member is formed of a rigid material having a linear configuration. The first boundary member is preferably formed of a shape memory alloy having a substantially parabolic preformed configuration and the second boundary member is preferably formed of stainless steel.

Further features of the surgical retractor of the subject invention will become more readily apparent from the following detailed description taken in conjunction with the drawings.

BRIEF DESCRIPTION OF THE DRAWINGS

So that one skilled in the art to which the subject invention appertains will understand how to make and use the invention, preferred embodiments of the surgical apparatus will be described hereinbelow with reference to the drawings wherein.

DETAILED DESCRIPTION OF THE PREFERRED EMBODIMENTS

The present invention shall be discussed in terms of endoscopic procedures and apparatus. However, use herein of terms such as "endoscopic" "endoscopically", and "endoscopic portion", among others, should not be construed to limit the present invention to an apparatus for use only in conjunction with an endoscopic tube. To the contrary, it is believed that the present invention may find use in procedures wherein access is limited to a small incision including but not limited to laparoscopic procedures.

In the drawings and in the description which follows, the term "proximal", as is traditional, will refer to the end of the apparatus which is closest to the operator, while the term "distal" will refer to the end which is furthest from the operator.

Figure 1:
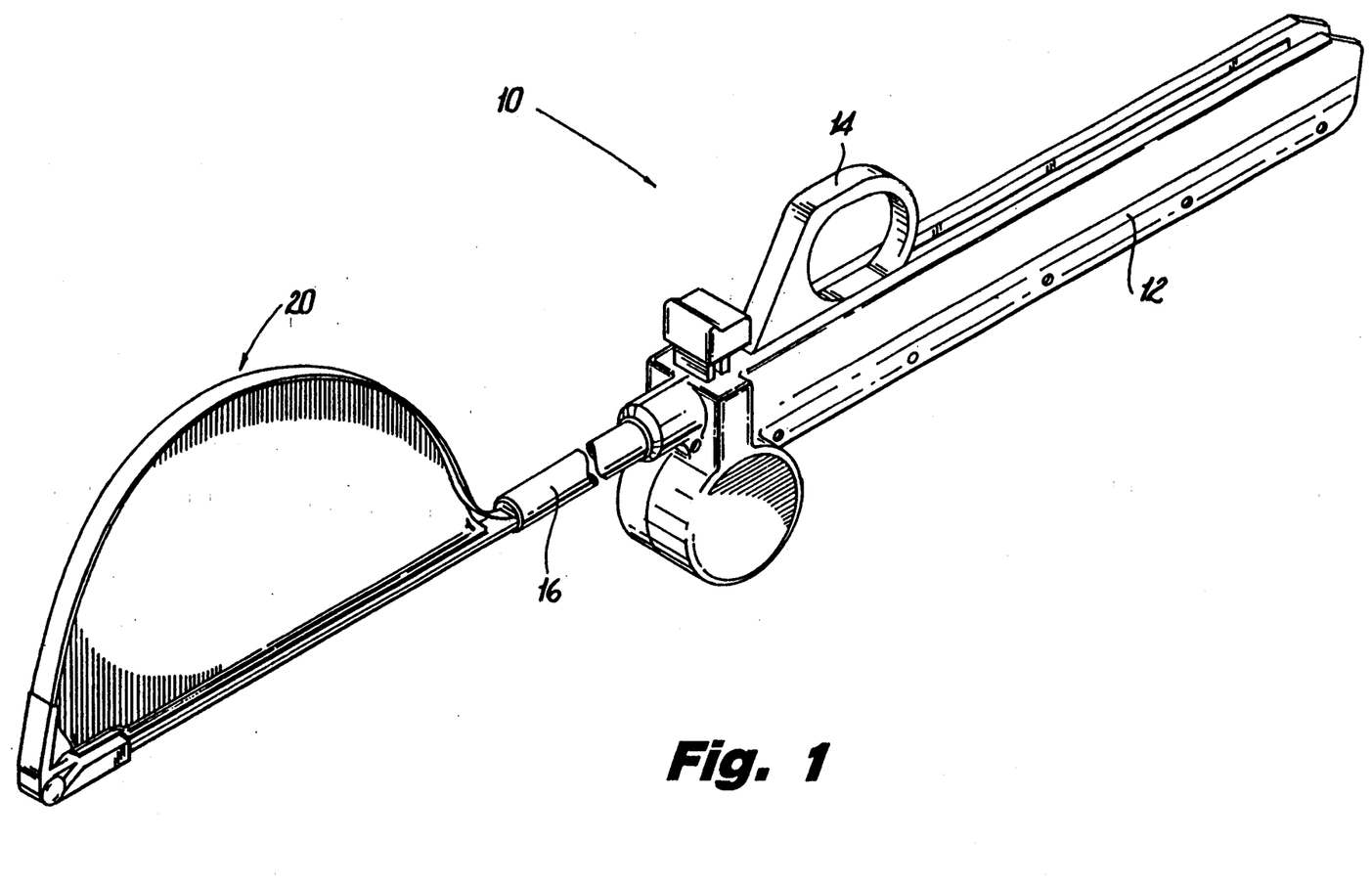
FIG. 1 is a perspective view of a surgical apparatus in accordance with a preferred embodiment of the subject invention.

Referring now in detail to the drawings, wherein like reference numerals identify similar structural elements, a surgical apparatus for performing retraction tasks during endoscopic or laparoscopic procedures in accordance with a preferred embodiment of the subject invention is illustrated in FIG. 1, and is designated generally by reference numeral 10. In brief, surgical apparatus 10 comprises an elongated handle portion 12 housing an actuator 14, an elongated tubular body portion 16 defining a longitudinal axis, and a retractor assembly 20 operatively associated with a distal end of body portion 16 and deployable through movement of actuator 14. The retractor assembly 20, which will be discussed in greater detail hereinbelow, preferably defines a curvilinear tissue manipulation surface having a selectively variable surface area which is particularly adapted for manipulating body tissue and large organs within the abdominal cavity during a surgical procedure.

Figure 2:
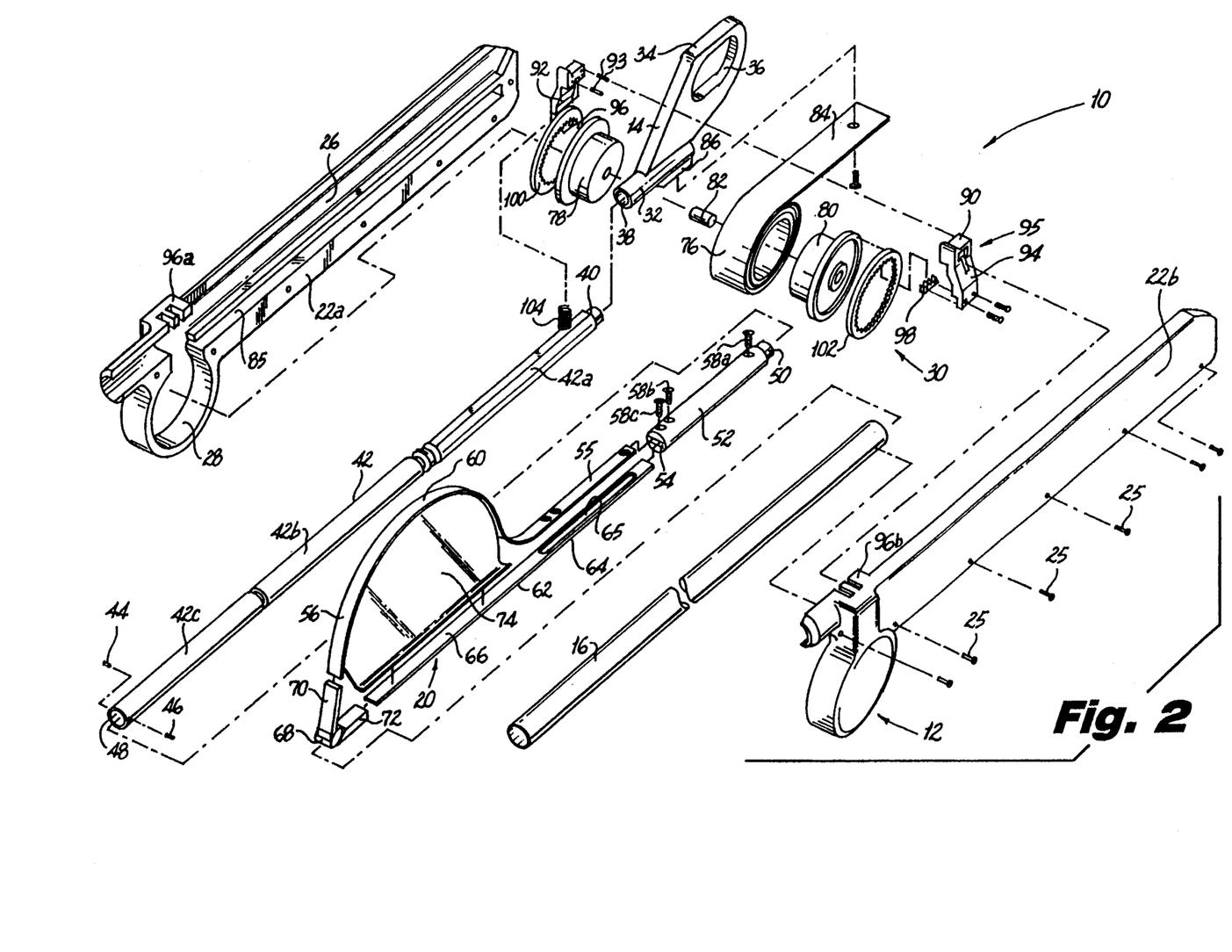
FIG. 2 is an exploded perspective view of the surgical apparatus of FIG. 1.

Referring to FIG. 2, the handle assembly 12 of surgical apparatus 10 includes handle hemi-sections 22a and 22b which are adapted to be assembled through the provision of a plurality of screw-type fasteners 25. Other methods of assembly are also envisioned, such as, for example, adhesive bonding, snap fit connections, or sonic welding. The handle hemisections may be constructed to be fully or partially removable or collapsible so as to maximize the surgical workspace and/or provide instrument stability.

Once assembled, the hemi-sections 22a and 22b of handle assembly 12 define an elongated passageway 26 for accommodating the axial translation of actuator 14, and a circular chamber 28 for housing an actuation control mechanism which is designated generally by reference number 30, and which will be described in greater detail hereinbelow. Actuator 14, which is operatively housed in handle assembly 12, comprises a guide portion 32 and a grasping portion 34 which defines a finger loop 36 for facilitating user manipulation of the apparatus. The guide portion 32 is particularly dimensioned to travel within the elongated passageway 26 and is formed with an axial retention bore 38 configured to engage and retain the proximal end 40 of an elongated, segmented, transmission rod 42.

Transmission rod 42, which is defined by a proximal segment 42a, a medial segment 42b, and a distal segment 42c, extends coaxially through the tubular body portion 16 of surgical apparatus 10 to the retractor assembly 20 which is associated with the distal end thereof. Alternatively, the transmission rod 42 may be of unitary construction, or it may be telescopically expandable along with the entire body portion 16 of surgical apparatus 10. A pair of set pins 44 and 46 are associated with the distal end 48 of the distal segment 42c of transmission rod 42 to maintain the proximal engaging end 50 of a tubular retention sleeve 52 which is associated with retractor assembly 20. More particularly, an elongated slot 54 extends through the tubular retention sleeve 52 for operatively receiving and supporting at least portions of the retractor assembly 20. With continuing reference to FIG. 2, retractor assembly 20 includes a first boundary member 56 of generally rectangular cross-section having a width that is substantially greater than the thickness thereof. Boundary member 56 is preferably formed of a resilient material, such as, for example, a shape memory alloy having a particular preformed configuration which is deformable when a stress is applied thereto and which will return to its original configuration when the stress is relieved. An example of a shape memory alloy is TINEL ® brand material which is available from Raychem Corporation. This alloy comprises a composition of nickel and titanium which exhibits the shape memory characteristics described hereinabove. Preferably, boundary member 56 has a curved preformed orientation of substantially parabolic configuration such that the retractor assembly 20 defines a curvilinear tissue manipulation surface. The curved configuration of boundary member 56 is particularly useful to retract large organs such as the large intestines for permitting easy access to other organs such as the small intestines. Boundary member 56 defines a proximal section 55 and a distal section 60. The proximal section 55 is operatively fastened within the elongated slot 54 formed in retention sleeve 52 by a plurality of screw-type fasteners including a proximal fastener 58a and spaced apart distal fasteners 58b and 58c. The distal section 60 of boundary member 56 delineates the curved periphery of the curvilinear tissue manipulation surface of retractor assembly 20.

Retractor assembly 20 further includes a second boundary member 62 which is also of substantially rectangular cross-section and which is preferably formed of a substantially rigid material, such as, for example, stainless steel. Boundary member 62 defines a proximal section 64 and a distal section 66. An elongated compensation slot 65 is formed in proximal section 64 to enable the translation of boundary member 56 relative to boundary member 62 as retention sleeve 52 translates while the retractor assembly 20 is deployed and withdrawn during operation (see generally, FIGS. 8 and 9). The relative translation of boundary members 56 and 62 will be discussed in greater detail hereinbelow. The distal section 66 of boundary member 62 delineates the linear periphery of the curvilinear tissue manipulating surface of retractor assembly 20. Preferably, the distal ends of boundary members 56 and 62 are operatively connected by a jointed coupling 68 which includes a first arm 70 for mounting the distal end of boundary member 56 and a second arm 72 for mounting the distal end of boundary member 62. The boundary members of retractor assembly 20 can be mounted to the arms of coupling 68 with heat activated shrink wrap materials, although other methods of mounting are also envisioned. Alternatively, the distal ends of boundary members 56 and 62 may be coupled directly to one another with any material of suitable flexibility, i.e. heat activated shrink wrap materials.

Figure 5:
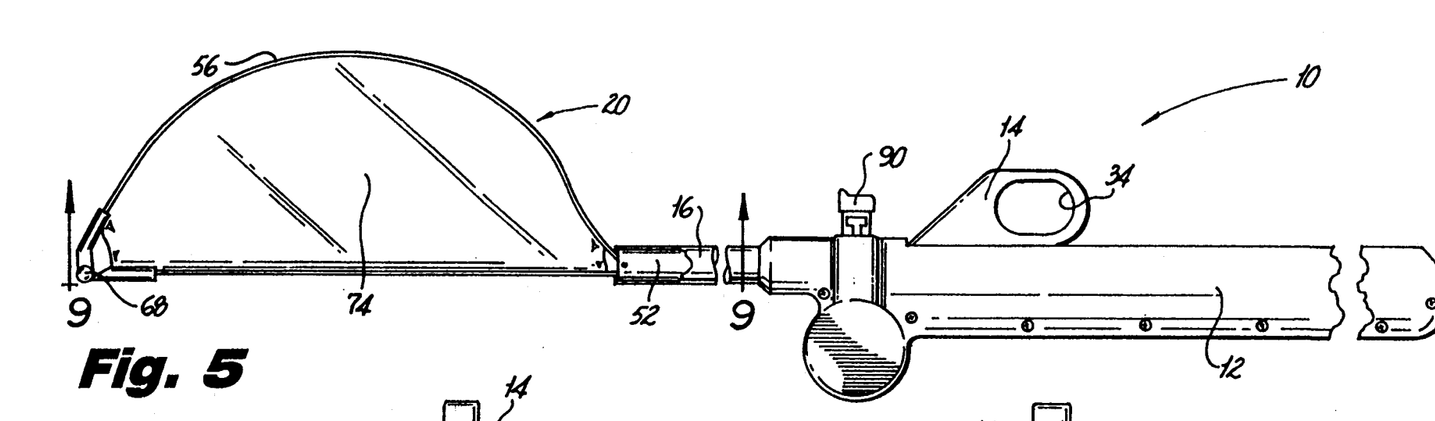
FIG. 5 is a side elevational view in cross-section of the surgical apparatus of FIG. 1 with the retractor assembly thereof in a fully deployed position;.
Figure 6:
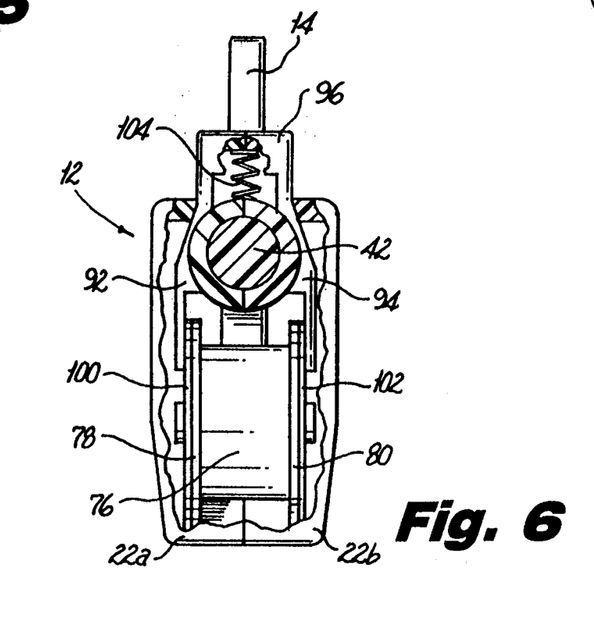
FIG. 6 is a cross-sectional view taken along line 6—6 of FIG. 3 with the braking mechanism in a disengaged position.

Retractor assembly 20 also includes membrane 74 which is preferably mounted to the internal surfaces of boundary members 56 and 62 and which substantially occupies the area bounded thereby. Membrane 74 is preferably formed of an elastomeric, polymeric or rubber material, such as, for example, latex and may be mounted to boundary members 56 and 62 by methods commonly known in the art, such as, for example, adhesive bonding. It is also envisioned that a flexible mesh can be utilized to define the tissue manipulation surface. In the alternative, a latex sheath may be removably disposed about the boundary members 56 and 62 which would be disposable after use. In use, the retractor assembly 20 of surgical apparatus is movable between the undeployed position of FIG. 3, wherein the area bounded by boundary members 56 and 62, occupied by membrane 74, and defining the curvilinear tissue manipulation surface is minimized, to the fully deployed position of FIG. 5, wherein the area defining the curvilinear tissue manipulation surface is maximized.

Referring again FIG. 2, the actuation control mechanism 30, which is housed within the circular cavity 28 defined in handle assembly 12 and which is provided to facilitate the deployment of retractor assembly 20, includes a constant force drum spring 76 which is mounted on a rotatable drum assembly including hub members 78 and 80 and an axle pin 82. The constant force drum spring 76 is normally biased in a counter-clockwise direction about axle pin 82 and includes an engaging end portion 84 which is accommodated within an elongated track 85 provided in handle assembly 12. The engaging end 84 of drum spring 76 is fastened to a flange 86 which depends from the guide portion 32 of actuator 14. As a result, the drum spring 76 serves to advantageously bias actuator 14 in a distal direction so that retractor assembly 20 is biased to the open or extended position. It will become apparent from the description which follows, that the distally directed bias of actuator 14 ultimately serves to enable one-handed operation of the surgical apparatus 10 of the subject invention.

Figure 3:
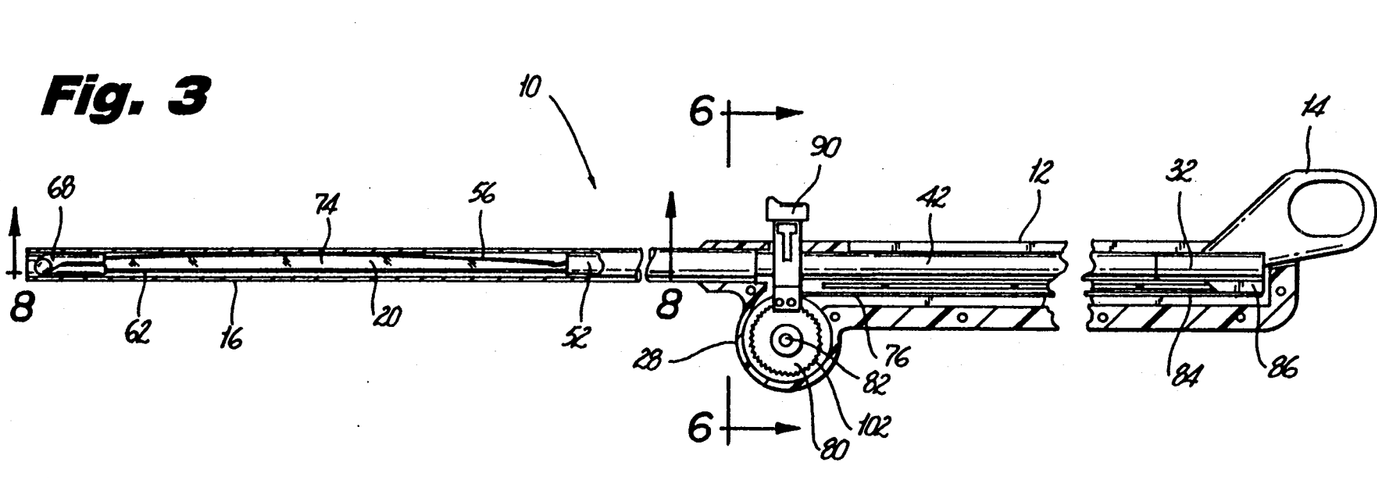
FIG. 3 is a side elevational view in cross-section of the surgical apparatus of FIG. 1 with the retractor assembly thereof in an undeployed position;.
Figure 4:
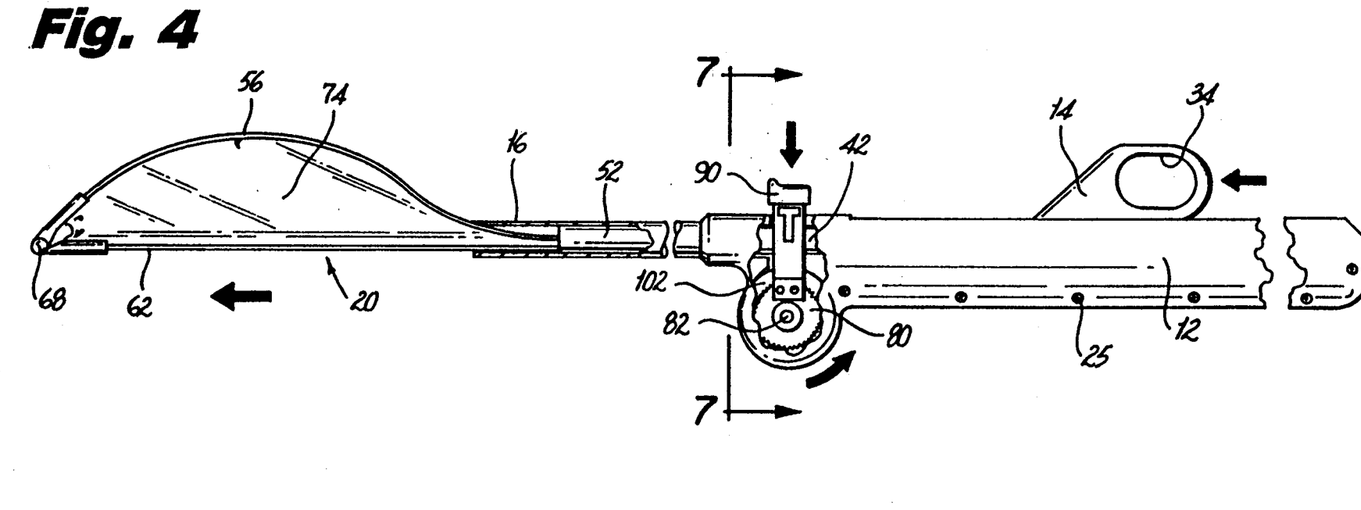
FIG. 4 is a side elevational view in cross-section of the surgical apparatus of FIG. 1 with the retractor assembly thereof in an partially deployed transitional position.
Figure 7:
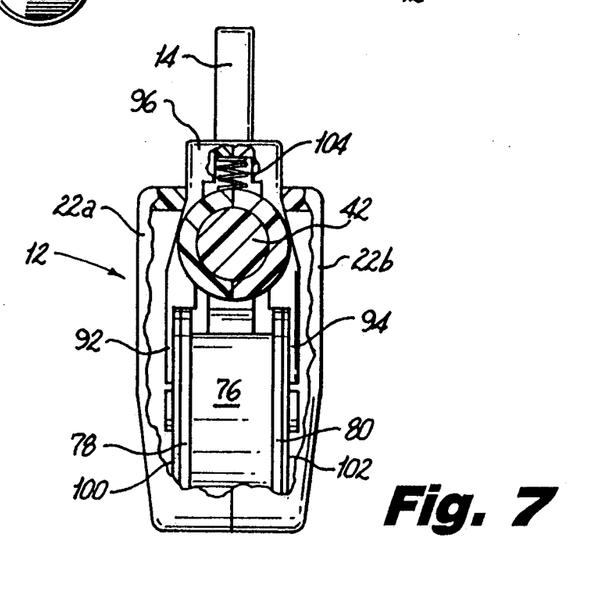
FIG. 7 is a cross-sectional view taken along line 7—7 of FIG. 4 with the braking mechanism in an engaged position.

Referring now to FIG. 2, in conjunction with FIGS. 3, 4, 6, and 7, surgical apparatus 10 further comprises a braking assembly 95 which is operatively associated with the actuation control mechanism 30 to effectuate the selective deployment of retractor assembly 20. The braking assembly 95 is movable between a first position, illustrated in FIG. 3, wherein the movement of the actuation control mechanism 30 is inhibited, and a second position, shown in FIG. 4, in which movement of the actuation control mechanism 30 is permitted. Braking assembly 95 includes a bifurcated yoke 90 comprising opposed yoke legs 92 and 94 connected by bridge pins 93 and mounted within slotted regions 96a and 96b formed in handle assembly 12. Yoke 90 has a button-like appearance to the user when apparatus 10 is fully assembled (see FIG. 5). Gear racks 96 and 98 are fastened to yoke legs 92 and 94, respectively, for cooperating with corresponding ring gears 100 and 102 which are mounted on hub members 78 and 80, respectively. Ring gears 100 and 102 are each formed with an internal race of gear teeth which are oriented in such a manner so as to permit the relative rotational movement of the ring gears in a first direction with respect to gear racks 96 and 98, i.e. when actuator 14 is withdrawn in a proximal direction to vary the configuration of retractor assembly 20, while inhibiting the relative rotational movement of the ring gears 100 and 102 in a second direction when they are engaged by the gear racks 96 and 98. In the alternative, a rack and pawl assembly could be provided to selectively permit rotation of the hub assembly. A coiled spring 104 is provided for biasing yoke 90 into the engaged position shown in FIGS. 3 and 6. In this position, the teeth of gear racks 96 and 98 are interengaged with the teeth of ring gears 100 and 102 to inhibit the rotation of hub members 78 and 80 and thus inhibit the distal translation of actuator 14 under the bias of barrel spring 76. To release the hub members 78 and 80, and permit the distal translation of actuator 14, the user may depress the yoke 90, compressing coil spring 104, and effectuating the respective disengagement of gear racks 96 and 98 from ring gears 100 and 102, as best seen in FIGS. 4 and 7.

Figure 8:
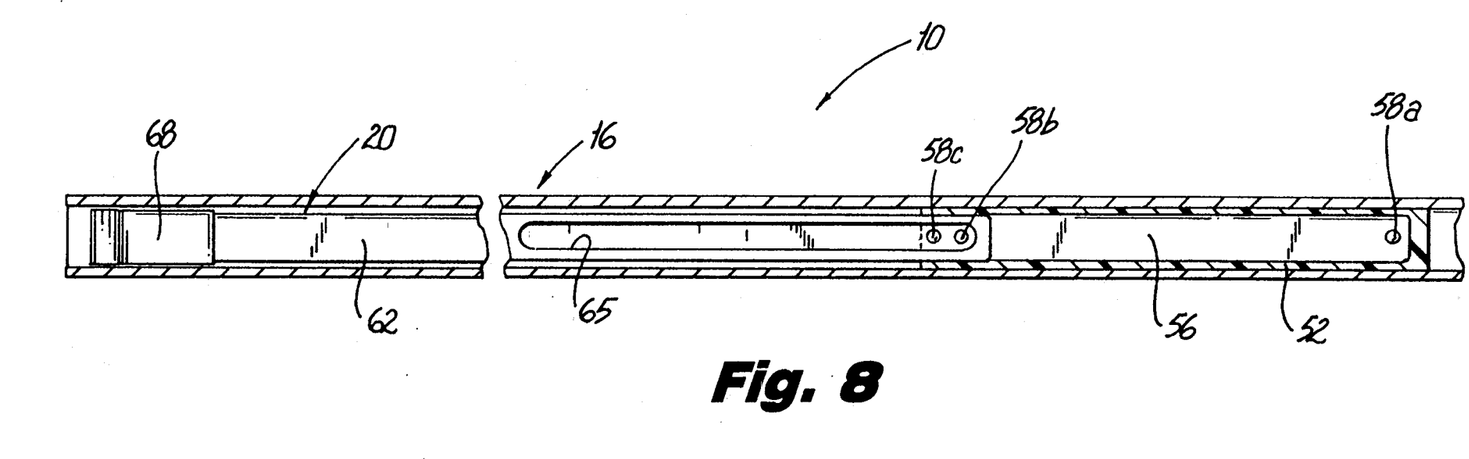
FIG. 8 is a cross-sectional view taken along line 8—8 of FIG. 3 with the retractor assembly in an undeployed position.

In operation, during a surgical procedure, the user may extend the body portion 16 of surgical apparatus 10 through a trocar or cannula device to introduce the instrument into the surgical site. Once the distal end of body portion 16 has been extended into the abdominal cavity, the retractor assembly 20, which is initially maintained within body portion 16 in a deformed stressed condition as seen in FIG. 3, may be deployed to effectuate the manipulation of body tissue or organs. As best seen in FIG. 8, in this undeployed position, the retention sleeve 52 of retractor assembly 20 is in its proximal most location within the body portion 16 of surgical apparatus 10. In this position, the spaced apart distal fasteners 58b and 58c are disposed adjacent the proximal end of the compensation slot 65 in boundary member 62.

Figure 9:
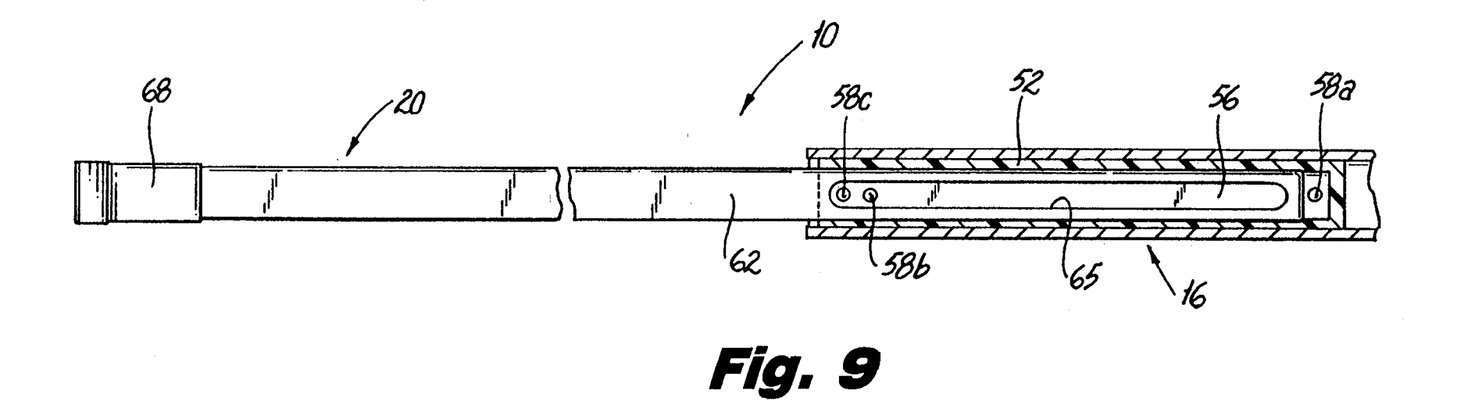
FIG. 9 is a cross-sectional view taken along line 9—9 of FIG. 5 with the retractor assembly in a fully deployed position.

To effectuate the movement of retractor assembly 20 from its undeployed position, the user may depress yoke 90, as illustrated in FIG. 4, to release the braking assembly 95 and permit the barrel spring 76 of actuation control mechanism 30 to draw actuator 14 in a distal direction. As actuator 14 translates under the influence of barrel spring 76, transmission rod 42 is also urged in a distal direction within body portion 16. As a consequence, the retention sleeve 52 is urged toward the distal end of body portion 16, initially driving boundary member 56 forward from the distal end of body portion 16. As boundary member 56 is protracted from body portion 16, stress is gradually relieved therefrom, permitting it to return to its preformed parabolic configuration. As a result, a resilient force is imparted on the portion of boundary member 56 remaining within body portion 16, tending to draw it from body portion 16. In addition, as boundary member 56 gradually conforms to its preformed configuration, membrane 74 is stretched to assume the selected configuration of the tissue manipulation surface. As retention sleeve 52 is urged toward the distal end of body portion 16, the fasteners 58b and 58c, which secure boundary member 56 thereto, translate distally within the compensation slot 65 of boundary member 62 until they are in contact with the distal end of the slot, as illustrated in FIG. 9, whereupon boundary member 62 will be urged forward to translate along with, and at the same rate as, boundary member 56. Although boundary member 62 is not fully spurred into motion until the fasteners 58b and 58c contact the distal end of compensation slot 65, it will initially translate distally at a rate which is less than that of the rate of deployment of boundary member 56 as coupling 68 is driven from the distal end of body portion 16.

At any time during the deployment stages of retractor assembly 20, the user may release the yoke 90 to reengage the brake mechanism and maintain the retractor assembly 20 in a desired configuration. Thereafter, the user may depress yoke 90 to release the brake mechanism, and permit retractor assembly 20 to move to a fully deployed position wherein the area of the curvilinear tissue manipulation surface bounded by boundary members 56 and 62 is maximized. At any time during the surgical procedure, the user may also alter the configuration of the retractor assembly 20 by drawing actuator 14 in a proximal direction, pulling therewith the engaging end 84 of barrel spring 76. Moreover, actuator 14 may be drawn in a proximal direction with or without depressing the yoke 90 to release the braking assembly 95.

It will be readily appreciated by those skilled in the art, that the surgical apparatus 10 of the subject invention is configured to facilitate one-handed actuation. Moreover, with only one hand, the user may deploy the retractor assembly 20 by releasing the braking mechanism with one finger, and reconfigure or withdraw the retractor assembly 20 by drawing actuator 14 proximally with another finger, thus leaving the second hand free to perform other surgical tasks.

Although the surgical apparatus of the subject invention has been described with respect to a preferred embodiment, it will be apparent to those skilled in the art to which the invention appertains that changes or modifications may be made thereto without departing from the spirit or scope of the invention as defined by the appended claims.

What is claimed is:

1. A surgical retractor for manipulating body tissue, comprising:
   a) a handle assembly;
   b) an elongated body extending from said handle assembly and defining a longitudinal axis; and
   c) a retractor assembly operatively with said body and defining a uniplanar curvilinear tissue manipulation surface having an area which is selectively variable, a periphery bounding said which is defined by first and second boundary members and an expandable membrane which solely occupies said area bounded by said boundary members, a distal end of said first boundary member being pivotably associated with a distal end of said second boundary member, said second boundary member being substantially collinear with said elongated body, and said retractor assembly being movable between a first position wherein the area of said tissue manipulation surface is minimized and a second position wherein the area of said tissue manipulation surface is maximized.

2. A surgical retractor as recited in claim 1, further comprising actuation means for progressively moving said retractor assembly between said first position and said second position.

3. A surgical retractor as recited in claim 1, further comprising biasing means for biasing said retractor assembly into said second position.

4. A surgical retractor as recited in claim 3, wherein said biasing means comprises a constant force drum spring.

5. A surgical retractor as recited in claim 3, further comprising control means for selectively controlling said biasing means to permit progressive movement of said retractor assembly from said first position to said second position.

6. A surgical retractor as recited in claim 5, wherein said control means comprises a selectively engagable ratchet assembly.

7. A surgical retractor as recited in claim 1, wherein said curvilinear tissue manipulation surface has a substantially paraboloidal configuration in at least one of said positions.

8. A surgical retractor as recited in claim 1, wherein said first boundary member is formed of a resilient material having a curved preformed configuration and said second boundary member is formed of a rigid material having a substantially linear configuration.

9. A surgical apparatus as recited in claim 1, wherein said first boundary member is formed of a shape memory alloy material having a substantially parabolic preformed configuration.

10. A surgical retractor as recited in claim 1, wherein said membrane comprises a flexible material selected from the group consisting of rubber, elastomers, and polymers.

11. A surgical retractor as recited in claim 10, wherein said membrane is formed of latex material.

12. A surgical retractor as recited in claim 1, wherein a pivot member operatively couples a distal end of each of said boundary members.

13. A surgical retractor for manipulating body tissue comprising:
   a) a handle assembly;
   b) an elongated body extending from said handle assembly and defining a longitudinal axis; and
   c) a retractor assembly operatively associated with said body and defining a curvilinear tissue manipulation surface having an area which is selectively variable, said retractor assembly including:

i) first and second boundary members defining a continuous periphery of said tissue manipulation surface, at least a portion of said periphery being substantially collinear with said longitudinal axis; and ii) a planar expandable member solely occupying the area bounded by said boundary members, said retractor assembly being movable between a first position wherein the area bounded by said boundary members is minimized and a second position wherein the area bounded by said boundary members is maximized.

14. A surgical retractor as recited in claim 13, wherein said first boundary member is formed of a resilient material having a substantially parabolic preformed configuration and said second boundary member is formed of a rigid material having a substantially linear configuration.

15. An endoscopic device adapted for one hand manipulation comprising:
a) a handle assembly;
b) an elongated tubular member extending from said handle assembly having a proximal end portion and a distal end portion;
c) at least one elongated member slidable within said elongated tubular member, said elongated member having a proximal end portion, a distal end portion, and being movable between a first proximal position and a second distal position;
d) a surgical tool disposed at the distal end of said elongated member;
e) at least one resilient biasing member disposed within said handle assembly and operatively connected to said elongated member, said biasing member adapted to urge said elongated member and said surgical tool from said first proximal position toward said second distal position, wherein said surgical tool is at least partially disposed distal of said elongated tubular member when said elongated member is in at least one of said positions; and
f) braking means for selectively preventing said biasing member from urging said elongated member toward said distal position, said elongated member configured to be stopped at a plurality of positions between said first and second positions.

16. An endoscopic device as recited in claim 15, wherein said surgical tool comprises a retractor.

17. An endoscopic device as recited in claim 15, further comprising means for releasing said braking means to allow said biasing member to urge said elongated member to move at least partially between said first and second positions.

18. An endoscopic device as recited in claim 16, wherein said means for releasing said braking means comprises a resiliently biased actuator disposed within said handle assembly.

19. An endoscopic device as recited in claim 15, wherein said at least one biasing member comprises a spring.

20. An endoscopic device as recited in claim 19, wherein said spring is a constant force spring.

21. An endoscopic device as recited in claim 15, wherein said braking means comprises a first gear member.

22. An endoscopic device as recited in claim 21, wherein said braking means further comprises a second gear member adapted to engage said first gear member.

23. An endoscopic device as recited in claim 22, wherein said second gear member is movable between first and second positions.

24. An endoscopic device as recited in claim 23, wherein said gear member in said first position prevents movement of said biasing member and said gear member in said second position permits movement of said biasing member.

25. An endoscopic device as recited in claim 22, wherein said means for releasing said braking means comprises a resiliently biased actuator disposed within said handle assembly and associated with at least one of said gear members.

26. An endoscopic device as recited in claim 25, wherein said resiliently biased actuator is a button protruding at least partially from said handle assembly.

27. An endoscopic device adapted for one hand manipulation comprising:
a) a handle assembly;
b) an elongated tubular member extending from said handle assembly having a proximal end portion and a distal end portion;
c) at least one elongated member slidable within said elongated tubular member, said elongated member having a proximal end portion, a distal end portion, and being movable between a first proximal position and a second distal position;
d) a surgical tool disposed at the distal end of said elongated member;
e) at least one resilient biasing member disposed within said handle assembly and operatively connected to said elongated member, said biasing member adapted to urge said elongated member and said surgical tool from said first proximal position toward said second distal position, wherein said surgical tool is at least partially disposed distal of said elongated tubular member when said elongated member is in at least one of said positions; and
f) actuating means for selectively controlling movement of said elongated member between said first and second positions.

28. An endoscopic device as recited in claim 27, wherein said actuating means comprises at least one gear member operatively associated with said resilient biasing member.

29. An endoscopic device as recited in claim 27, wherein activation of said actuation means permits movement of said elongated member and deactivation of said actuation means prevents movement of said elongated member.

30. An endoscopic device as recited in claim 29, wherein said actuation means is deactivated when in a static state and is activated by application of pressure.

* * * * *